United States Patent
Velardi et al.

(10) Patent No.: US 6,521,788 B2
(45) Date of Patent: Feb. 18, 2003

(54) PROCESS FOR THE PREPARATION OF 1-AMINOMETHYL-1-CYCLOHEXANEACETIC ACID

(75) Inventors: Francesco Velardi, Cameri (IT); Mirco Fornaroli, Cameri (IT)

(73) Assignee: Procos S.p.A., Cameri (IT)

( * ) Notice: Subject to any disclaimer, the term of this patent is extended or adjusted under 35 U.S.C. 154(b) by 0 days.

(21) Appl. No.: 10/156,059

(22) Filed: May 29, 2002

(65) Prior Publication Data

US 2003/0009055 A1 Jan. 9, 2003

(30) Foreign Application Priority Data

May 29, 2001 (IT) .......................... MI01A1132

(51) Int. Cl.$^7$ .............................. C07C 61/08
(52) U.S. Cl. ...................... 562/507; 543/558
(58) Field of Search ................. 562/507; 548/543, 548/558

(56) References Cited

U.S. PATENT DOCUMENTS

| | | |
|---|---|---|
| 4,024,175 A | 5/1977 | Satzinger et al. |
| 4,087,544 A | 5/1978 | Satzinger et al. |
| 4,894,476 A | 1/1990 | Butler et al. |
| 5,091,567 A | 2/1992 | Geibel et al. |

OTHER PUBLICATIONS

DiBiase, S. et al., "Direct Synthesis of α, β–Unsaturated Nitriles from Acetonitrile and Carbonyl Compounds: Survey, Crown Effects, and Experimental Conditions", *J. Org.Chem.*, vol. 44, No. 25, 1979, pp. 4640–4649.

DiBiase, S. et al., "A Convenient Synthesis of Aliphatic χ, β–Unsaturated Nitriles from Acetonitrile", *Synthesis*, Sep. 1977, pp. 629–631.

*Primary Examiner*—Paul J. Killos
(74) *Attorney, Agent, or Firm*—Young & Thompson

(57) ABSTRACT

A process for the preparation of gabapentin of formula (I)

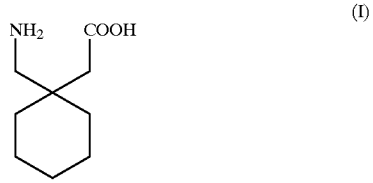

which comprises:

a) reduction of (1-nitromethyl-cyclohexyl)acetonitrile of formula (II)

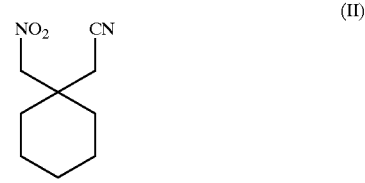

to give 3-imino-2-aza-spiro[4.5]decan-2-ol of formula (III)

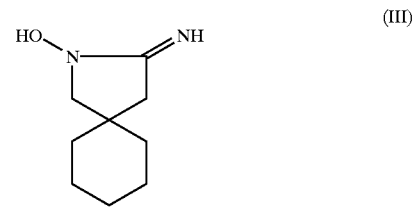

b) transformation of compound (III), by alkali treatment, into 2-hydroxy-2-aza-spiro[4.5]decan-3-one of formula (IV)

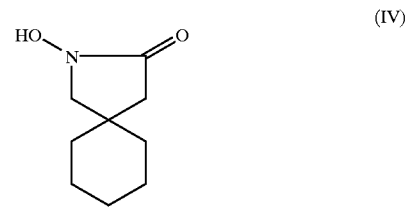

c) reduction of compound (IV) to give 2-aza-spiro[4.5]decan-3-one of formula (V)

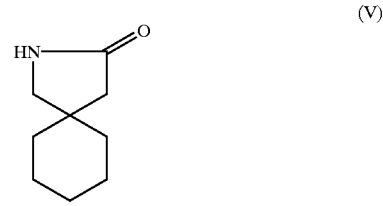

d) hydrolysis of compound (V) to gabapentin.

7 Claims, No Drawings

PROCESS FOR THE PREPARATION OF 1-AMINOMETHYL-1-CYCLOHEXANEACETIC ACID

The present invention relates to a process for the preparation of gabapentin.

Gabapentin, namely 1-aminomethyl-1-cyclohexaneacetic acid, of formula (I)

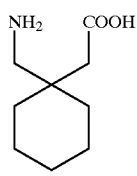
(I)

a medicament widely used in the treatment of pathologies of Central Nervous System, is disclosed in U.S. Pat. Nos. 4,024,175 and 4,087,544.

Said patents disclose the hydrate hydrochloride salt, while gabapentin hydrate sodium salt is disclosed in U.S. Pat. No. 4,894,476.

A variety of processes for the preparation of gabapentin are known: for example, the conversion of 1,1-cyclohaxanediacetic acid to gabapentin by treatment with azides and thermal degradation according to Curtius has been described.

Another known method includes subjecting the corresponding hydroxamic acid to Lossen rearrangement.

U.S. Pat. No. 5,091,567 discloses a process based on Michael condensation between cyclohexanone and a phosphonoacetic acid ester, the subsequent reaction with nitromethane to give the cyclohexylideneacetic acid ester, the reduction of the nitro group to give a mixture of gabapentin ester and of the corresponding lactam (2-aza-spiro[4.5]decan-3-one), the acid hydrolysis of the latter and the treatment of the gabapentin salt with ion exchange resins.

An improved process has now been found, wherein the phosphonoacetic acid ester is replaced with the more convenient acetonitrile, and wherein the formation of a mixture of gabapentin and corresponding lactam is avoided.

The process of the invention comprises:

a) reduction of (1-nitromethyl-cyclohexyl)acetonitrile of formula (II)

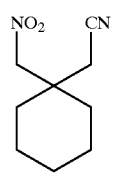
(II)

to give 3-imino-2-aza-spiro[4.5]decan-2-ol of formula (III)

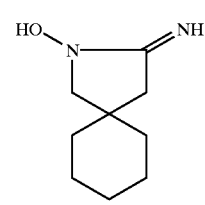
(III)

b) transformation of compound (III), by alkali treatment, into 2-hydroxy-2-aza-spiro[4.5]decan-3-one of formula (IV)

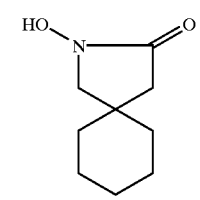
(IV)

c) reduction of compound (IV) to give 2-aza-spiro[4.5]decan-3-one of formula (V)

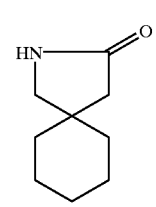
(V)

d) hydrolysis of compound (V) to gabapentin.

The invention further relates to the novel intermediates of formulae (III) and (IV), which are up to now unknown.

The compound of formula (II) was disclosed in WO 99/31075 and can be prepared by reaction of cyclohexylideneacetonitrile and nitromethane in a solvent such as dimethylsulfoxide in the presence of bases, for example alkali carbonates.

Cyclohexylideneacetonitrile can in turn be obtained by reacting cyclohexanone and acetonitrile according to what described in Synthesis 629, 1977 and in J.Org.Chem., 4640, 1979.

Step a) is preferably effected by catalytic hydrogenation, for example over palladium, using solvents selected from alcohols, ethers, esters, hydrocarbons, halogenated hydrocarbons. Preferred solvents are methanol or ethanol.

Compound (III) is converted into compound (IV) by treatment with bases, such as aqueous alkali hydroxides.

Step c) is carried out by catalytic hydrogenation, preferably using a nickel catalyst and an alcohol as solvent.

Finally, hydrolysis of compound (V) to Gabapentin is effected according to known methods, for example by acid hydrolysis.

The following examples illustrate the invention in greater detail.

EXAMPLES

A) Preparation of Cyclohexylideneacetonitrile

A 10 l round-bottom flask is loaded with 285 g (4.57 mols) of 90% potassium hydroxide in flakes and 1775 ml of hexane. The mixture is heated to 55° C. and, keeping heating, a solution consisting of 450 g (4.59 mols) of cyclohexanone and 1351 ml of acetonitrile is quickly dropped therein (during the addition temperature falls to 52.6° C.). The mixture is refluxed for 7 hours, then cooled at room temperature. 2863 ml of water are added thereof to dissolve the solid. The organic phase is washed twice with water (1000 ml each). The phases are separated and the organic phase is evaporated to dryness under vacuum, to obtain 462 g of a residue which is distilled under 10 mmHg at 100–105° C.

305.3 g of distillate are obtained. GC 87.5% isomer: 9.4%.

B) Preparation of Compound (II) (1-nitromethyl-cyclohexyl)-acetonitrile

A 1000 ml round-bottom flask is loaded with 18.1 g (0.131 mols) of dry potassium carbonate, 140 ml of dimethylsulfoxide, 36 g (0.266 mols) of 89.7% cyclohexylideneacetonitrile, 25.3 g (0.398 mols) of 96% nitromethane. The mixture is heated at 95° C. for 10 hours, then cooled with ice-water and dropwise added with 43 ml of 30% hydrochloric acid. The mixture is stirred for 10' and added with 145 ml of water (exothermic reaction) and 110 ml of isopropyl ether. After stirring for 10', the phases are separated and the aqueous phase is extracted again with 70 ml of isopropyl ether. The ether extracts are combined and washed twice with water (70 ml each), then the organic phase is evaporated to dryness under vacuum, to obtain 50.5 g of a residue: GC:83.2% (cyclohexylideneacetonitrile: 7.7%; isomer: 5.8%); Yield: 86.7%.

C) Preparation of Compound (III) 3-imino-2-aza-spiro[4.5]decan-2-ol

A 1.8 l autoclave, equipped with electronic manometer, continuous recording thermocouple and muffle heating, is loaded at room temperature with 124 g (0.578 mols) of 85% compound (II), 15 g of 10% dry Pd/C and 1000 ml of absolute ethanol. After washing with nitrogen, stirring is started, then hydrogen is fed under about 40 bars. Hydrogen is fed again when pressure reaches 35 bars.

After hydrogenating for 6 hours, hydrogen is discharged, washing three times with nitrogen and the autoclave is discharged twice with absolute ethanol, 300 ml each. The catalyst is filtered off and the filtered solution is concentrated, first under reduced pressure and then, when stirring becomes difficult, under atmospheric pressure to 160 ml final volume (maximum internal temperature 87° C.). The mixture is cooled to 50° C. and added with 285 ml of acetone, then cooled and left at 0 to +5° C. for 1 hour. The mixture is filtered washing with acetone and dried under atmospheric pressure at 50° C. overnight. 65.1 g of the title compound are obtained (m.p. 240° C. (dec.))—HPLC 99.4%.

NMR:

Proton spectrum in $CD_3OD$ (chemical shifts are expressed in ppm with tetramethylsilane as internal reference)

| Chemical shifts | Multiplicity | Integration | Assignment |
|---|---|---|---|
| 1.5–1.6 | m | 10 H | Cyclohexyl methylenes |
| 2.23 | s | 2 H | methylene |

| Chemical shifts | Multiplicity | Integration | Assignment |
|---|---|---|---|
| 3.4 | s | 2 H | —$CH_2N$— |

Carbon-13: 22.6 ($CH_2$); 25.5 ($CH_2$); 34.1 (C quaternary); 37.2 ($CH_2$); 47.6 ($CH_2$—CO); 60.7 ($CH_2$—N); 169.5 (CON)

IR bands:

| Frequency ($cm^{-1}$) | Assignment |
|---|---|
| 3202 | ν OH o ν NH |
| 2921–2856 | ν $CH_2$ |
| 1707 | ν C=N |
| 1449 | $CH_2$ scissor |
| 1211 | δ NOH |

D) Preparation of Compound (IV) 2-hydroxy-2-aza-spiro[4.5]decan-3-one 50.5 g (296 mmoles) of compound (III) (98.6% HPLC), 130 g of 30% NaOH and 26 g of water are refluxed for 1 hour, then cooled with stirring to precipitate a solid. 105 ml of conc. hydrochloric acid are dropped therein without exceeding 30° C., checking pH which should be 1 or lower at the end of the addition. During the addition the solid first dissolves, then a white solid finally precipitates again. The mixture is kept under stirring for 45 minutes at 4° C., them filtered without washing. The humid solid is added with 100 ml of water and kneaded for approximately 60 minutes at 4° C., then filtered, washed with water (30 ml), finally dried at 40° C. in oven under atmospheric pressure overnight.

37.2 g of the title compound are obtained [74.3% on theoretical] (HPLC 99.6%).

Chemical titre: 97.4%

M.p.: 110° C.

NMR:

Proton spectrum in $CD_3OD$ (chemical shifts are expressed in ppm with tetramethylsilane as internal reference)

| Chemical shifts | Multiplicity | Integration | Assignment |
|---|---|---|---|
| 1.3–1.7 | m | 10 H | Cyclohexyl methylenes |
| 2.55 | s | 2 H | methylene |
| 3.55 | s | 2 H | —$CH_2N$— |

Carbon-13: 22.4 ($CH_2$); 24.8 ($CH_2$); 35.5 (C quaternary); 36.4 ($CH_2$); 39.5 ($CH_2$); 66.0($CH_2$); 105.5(C=N)

IR bands:

| Frequency ($cm^{-1}$) | Assignment |
|---|---|
| 3122 | ν OH |
| 2925–2845 | ν $CH_2$ |
| 1669 | ν C=O |
| 1532 | δ OH |
| 1448 | $CH_2$ scissor |
| 1063 | ν NO |

E) Preparation of Compound (V) 2-aza-spiro[4.5]decan-3-one

A 1.8 l autoclave equipped with electric manometer, continuous recording thermocouple and muffle heating, is loaded at room temperature with 130 g (0.768 m) of compound (IV), 1300 ml of methanol and 10 g of nickel Raney. After washing with nitrogen, stirring is started, while thermostating at 80° C., and hydrogen is fed under 40 bars. After hydrogenating for 3 hours, the hydrogen pressure is discharged, washing three times with nitrogen, and the autoclave is discharged washing with 500 ml of methanol. The catalyst is filtered off and the mixture is evaporated to dryness, to obtain 109.8 g of the title compound (HPLC: 99.9%)

F) Preparation of Gabapentin Hydrochloride 2 g (13 mmoles) of compound (V), 10 ml of water and 10 ml of conc. hydrochloric acid are refluxed for 4 hours. The mixture is cooled and washed twice with methylene chloride (10 ml each). The combined organic phases are evaporated to dryness under vacuum, to obtain 0.5 g of compound (V), 90% (HPLC). The aqueous phase is evaporated to dryness under vacuum, to obtain 2.4 g of a deliquescent solid, which is taken up with 10 ml of acetone and triturated for 15 minutes, then filtered without washing (residue of filtration after evaporation to dryness=0.1 g). After drying at 40° C. under atmospheric pressure overnight, 1.7 g of the title compound are obtained (HPLC 99.6%) (yield 73%).

G) Preparation of Gabapentin

A chromatographic column is loaded with 385 g of AMBERLITE IRA 67®, eluting first with 1000 ml of 12% NH3, then with 6000 ml of purified water to neutral pH of the eluate. After that, Gabapentin hydrochloride, 78.5 g (378 mmoles) dissolved in 320 ml of purified water is loaded on the column, eluting with 2000 ml of purified water.

The eluate is filtered through paper and dried under reduced pressure, azeotropically removing water with isopropyl ether. The hot residue is dissolved with 560 ml of methanol, insoluble are filtered off while hot and the solution is evaporated to dryness under reduced pressure. The residue is dissolved in 150 ml of acetone, stirring for 1 hour, the filtered at 0° C. The residue is dried under atmospheric pressure at 40° C. and under reduced pressure for 4 hours.

53 g of the title compound are obtained (yield 81.8%).

What is claimed is:

1. A process for the preparation of gabapentin of formula (I)

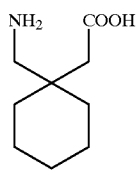

which comprises:
a) reduction of (1-nitromethyl-cyclohexyl)acetonitrile of formula (II)

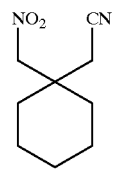

to give 3-imino-2-aza-spiro[4.5]decan-2-ol of formula (III)

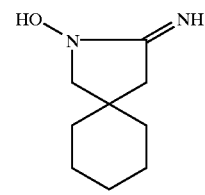

b) transformation of compound (III), by alkali treatment, into 2-hydroxy-2-aza-spiro[4.5]decan-3-one of formula (IV)

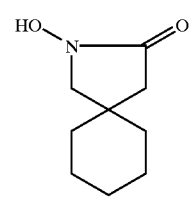

c) reduction of compound (IV) to give 2-aza-spiro[4.5]decan-3-one of formula (V)

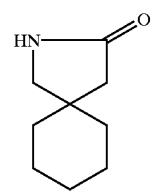

d) hydrolysis of compound (V) to gabapentin.

2. A process as claimed in claim 1, in which step a) is carried out by catalytic hydrogenation.

3. A process as claimed in claim 1, in which step b) is effected by treatment with aqueous alkali hydroxides.

4. A process as claimed in claim 1, in which step c) is effected by catalytic hydrogenation.

5. A process as claimed in claim 1, in which hydrolysis of compound (V) is carried out by treatment with acids.

6. A compound of formula (III)
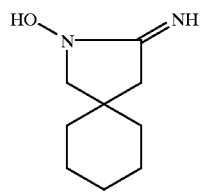
(III)
7. A compound of formula (IV)
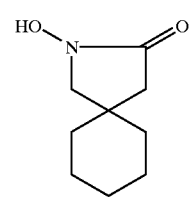
(IV)
* * * * *